US012714465B1

(12) United States Patent
Thompson

(10) Patent No.: US 12,714,465 B1
(45) Date of Patent: Aug. 25, 2026

(54) FIRST TWIN CERVICAL DILATION SYSTEM AND METHOD

(71) Applicant: Stephen W. Thompson, Naples, FL (US)

(72) Inventor: Stephen W. Thompson, Naples, FL (US)

( * ) Notice: Subject to any disclaimer, the term of this patent is extended or adjusted under 35 U.S.C. 154(b) by 0 days.

(21) Appl. No.: 19/332,975

(22) Filed: Sep. 18, 2025

Related U.S. Application Data

(60) Provisional application No. 63/696,630, filed on Sep. 19, 2024.

(51) Int. Cl.

| | |
|---|---|
| ***A61M 29/00*** | (2006.01) |
| ***A61B 17/42*** | (2006.01) |
| ***A61L 29/06*** | (2006.01) |
| ***A61L 29/08*** | (2006.01) |
| ***A61M 25/10*** | (2013.01) |
| ***A61M 29/02*** | (2006.01) |
| *A61B 17/00* | (2006.01) |

(52) U.S. Cl.

CPC .............. *A61B 17/42* (2013.01); *A61L 29/06* (2013.01); *A61L 29/085* (2013.01); *A61M 25/1002* (2013.01); *A61M 25/10182* (2013.11); *A61M 25/10187* (2013.11); *A61M 29/02* (2013.01); *A61B 2017/00557* (2013.01); *A61B 2017/00831* (2013.01); *A61B 2017/00845* (2013.01); *A61B 2017/4225* (2013.01); *A61L 2400/10* (2013.01); *A61M 2025/1093* (2013.01); *A61M 2205/3344* (2013.01); *A61M 2205/3379* (2013.01); *A61M 2210/1433* (2013.01); *A61M 2210/1475* (2013.01)

(58) Field of Classification Search

CPC .............. A61B 17/42; A61B 17/12022; A61B 17/12027; A61B 17/12099; A61M 2025/102; A61M 2025/1022; A61M 2025/1093; A61M 2025/1088; A61M 2025/1043; A61M 2025/1047; A61M 25/1018; A61M 25/10184; A61M 25/10187; A61M 25/10188; A61M 25/1002

See application file for complete search history.

(56) References Cited

U.S. PATENT DOCUMENTS

| | | | |
|---|---|---|---|
| 5,947,991 | A | 9/1999 | Cowan |
| 10,512,760 | B2 | 12/2019 | Harpaz et al. |
| 10,660,670 | B1 | 5/2020 | Niver |

(Continued)

*Primary Examiner* — Tuan V Nguyen

(74) *Attorney, Agent, or Firm* — John Rizvi; John Rizvi, P.A.—The Patent Professor®

(57) ABSTRACT

An active labor assistant system includes a cervix, vaginal, vaginal introitus (entire birth canal) dilator. The birth canal dilator includes a shaft extending along a longitudinal axis. The shaft defines a passageway. A balloon includes a proximal end coupled to the shaft and a distal end that is coaxial with the longitudinal axis. The balloon defines a chamber that is in communication with the passageway. The shaft is configured to be coupled to an inflation source to move an inflation material through the passageway and into the chamber to move the balloon between an uninflated configuration in which the distal end of the balloon has a convex orientation an inflated configuration for insertion in which the distal end of the balloon has a concave orientation.

20 Claims, 11 Drawing Sheets

(56) References Cited

U.S. PATENT DOCUMENTS

| | | | | |
|---|---|---|---|---|
| 2008/0077054 | A1 | 3/2008 | Feuer et al. | |
| 2008/0319472 | A1* | 12/2008 | Shelley | A61M 29/02 606/193 |
| 2013/0245664 | A1 | 9/2013 | Niver | |
| 2016/0183977 | A1* | 6/2016 | Marshburn | A61B 17/4241 606/191 |
| 2017/0143944 | A1 | 5/2017 | Harpaz et al. | |
| 2021/0106458 | A1* | 4/2021 | Bacich | A61F 6/146 |

* cited by examiner

FIRST TWIN CERVICAL DILATION SYSTEM AND METHOD

CROSS-REFERENCE TO RELATED APPLICATION

This application claims the benefit of U.S. Provisional Patent Application Ser. No. 63/696,630 filed Sep. 19, 2024, which is incorporated herein in its entirety.

FIELD OF THE INVENTION

The present invention relates generally to the process of labor and delivery-a woman giving birth to her child. Prior art includes more than one technique of cervical ripening (or softening). This invention is not intended to assist in cervical ripening which may lead to active labor. This invention is an improvement to active labor, which is needed to safely and more easily complete the entire process of labor and delivery, which may include cervical ripening, which is the softening and thinning of the cervical dilation system of a balloon catheter configured to stimulate the cervical dilation caused by a first twin, that completely opens the entire configured Birth Pathway to simulate the cervical dilation cause by a first twin, that completely opens the entire birth canal, thus making the passage for the second twin faster much easier and safer for mother and baby.

BACKGROUND OF THE INVENTION

Obstetrical induction and/or augmentation of labor by dilation of the cervix vagina, pelvic muscles and vaginal introitus. Anatomically this comprises the entire birth canal and the action of dilation from uterine contractions propelling the baby through the birth canal which is referred to as active labor. Prior art discloses methods of softening thinning and a small bit of dilation also referred to as latent phase labor or cervical ripening, which is a process of softening the cervix to stimulate dilation and prepares the cervix for contractions and labor induction. Conventional induction techniques may include nonpharmacologic approaches, medication, mechanical dilators or other procedures. Some unconventional pharmacologic and nonpharmacologic approaches to cervical ripening and labor induction include herbal compounds oils and/or derivatives, castor oil, hot baths, enemas, sexual intercourse, breast stimulation, acupuncture, acupressure, transcutaneous nerve stimulation. Some medication available for cervical ripening and labor induction include prostaglandins, misoprostol, mifepristone, and relaxin. However, the mechanical and surgical methods (mechanical dilators) can be more effective for cervical ripening or induction of labor than pharmacologic approaches or medication.

Conventional mechanical dilators include balloon catheters. However, balloon catheters have only been used to dilate the cervix approximately 1-2 cm in the past and even after cervical ripening and currently available methods of induction there is a 33% failure rate ending up resorting to C-Sections. Accordingly, there is a need for a solution to at least one of the aforementioned problems. For instance, there is an established need for a cervical dilation system and method that simulates the dilation caused by a first twin to allow a baby to slide easily through a dilated birth canal.

SUMMARY OF THE INVENTION

The present invention is directed to a cervical dilation system and method of use for labor and delivery. The cervical dilation system includes a cervical dilator, such as, for example, a cervical dilator balloon catheter that can be expanded to large diameters. The balloon of the balloon catheter can be made from silicon rubber, for example. The balloon of the balloon catheter may be inflated to expand the cervix to induce and complete labor, which makes labor shorter with less complications. Indeed, the longer labor takes, the greater the risk for bleeding, infection, etc. It is therefore beneficial to decrease the amount of time required for labor. Use of the cervical dilator of the present disclosure can thus pose less of a medical risk than use of hormones for dilation, due to the reduced amount of time it takes to complete labor using the cervical dilator of the present disclosure. It is envisioned that the cervical dilator of the present disclosure can also decrease the need for a C-section, as discussed in greater detail hereinbelow. While Foley catheters have been utilized for cervical ripening, cervical ripening is only to soften, thin and provide a small amount of dilation. The cervical dilation system of the present disclosure, in contrast, is adapted to assist in active labor and delivery (dilation from 3-10 cm), which includes dilating the vagina, introitus and pelvic muscles and is not provided by cervical ripening.

Use of the cervical dilation system of the present disclosure can generally include inserting a cervical dilator into a mother's cervix when the mother is approximately 1-3 cm dilated; inflating the balloon with saline to further dilate the mother's cervix to approximately 3-5 cm; retracting the inflated balloon to further dilate the cervix and birth canal, then deflating the balloon by removing the saline; removing the deflated balloon from the mother's cervix; reinserting the deflated balloon into the mother's cervix; reinflating the deflated balloon with saline to further dilate the mother's cervix (to approximately 10 cm) and complete labor. It is envisioned that after utilizing the cervical dilation system of the present disclosure delivery can be done in approximately 30 minutes with little effort. Without this process, pushing commonly takes 2-3 hours or more contributing to high C-Section rates of more than 33%. This streamlined labor and delivery method is a great improvement over conventional methods. The dilation system of the present disclosure may reduce the total labor process from 24-72 hours down to 4-8 hours for first-time pregnancies.

More specifically, use of the cervical dilation system of the present disclosure can include softening the cervix with or without medication such as cervidil for approximately 3-8 hours. Then the large conical balloon of the balloon catheter is inserted into the patient's cervix. The conical balloon can be narrow at the bottom and wide and spherical at the top. The conical balloon is inserted after the cervix is 1-3 cm with optional prostaglandin or optional double cervical balloon catheter or single urinary catheter balloon. For labor and delivery, the conical balloon can include a 10 cm diameter at the top with contoured soft top surface and below a narrow dilating conical stem. Prior to inflation, the catheter is 1 cm at the distal tip for insertion, and when fully inflated, it is 10-12 cm at the top and 2-3 cm at the bottom. A pressure gauge and/or volume meter may optionally be used to measure pressure and volume. An electric or manual inflation pump or 20-50 or 100 cc syringe can be used to fill the balloon such that the balloon expands/inflates. During the first 3 to 8 hours of the labor process, the deflated device is repeatedly inserted then inflated and then gently removed 1 to 3 times resulting in full dilation to 10-12 cm of the cervix, vagina and vaginal introitus (entire birth canal). The patient can now easily push the baby out through the fully dilated birth canal with the least amount of force on the baby, mother, and the birth canal.

During the insertion, inflations and withdrawals of the inner conical dilating balloon, the balloon passes through an outer loose 2 layered sheath/sleeve with a lubricant of silicone or other lubricant having an extremely low coefficient of friction located between the outer and inner layers of the sheath. This 2 layered sleeve is constructed of low friction materials such as polyethylene and it is 11 cm in diameter with a small amount of lubricant contained in the space between the inner and outer layers with the low friction coefficient interfaces and lubricant to allow the balloon to propel through the birth canal smoothly with the least amount of friction or pressure. Once the fully inflated balloon has passed through the birth canal, the birth canal will remain dilated for the mother to push the baby through the dilated cervix, vagina and introitus.

Typically, cervical ripening may take 1-2 hours. 3-6 hours or more of pitocin may be administered to the patient. The cervical dilation system can include a silicone liquid lubricator and other lubrication for vaginal lubrication similar to Astroglide or other water-soluble lubricant. Cervical dilation can take 2-4 hours to complete using the system and method of the present disclosure. The system and method of the present disclosure can include use as an introital dilator by pulling the inflated conical balloon through the vagina simultaneously with the cervix dilation. Lubricating and dilating the vagina is continued. Vacuum assist should not be needed. In the event a vacuum assist is used, using low negative pressures is recommended and should have no more than 1 or 2 pulls with 2 contractions and maternal pushes. Use of modified Oden extractor should not be necessary but is permissible. A modified Oden extractor with a soft tubular balloon 3-4 cm rim around the head circumference below the crown can be used to draw the baby out through the birth canal pathway that is opened using the cervical dilation system.

In some embodiments, use of the cervical dilation system of the present disclosure can include inserting an IV and administering an IV antibiotic for prophylaxis to prevent infection; and maintaining IV for hydration during labor and delivery. The patient is attached to a continuous fetal monitor. A physical exam is performed to estimate fetal weight and position. Epidural anesthesia is obtained for comfort during labor and insertion/retraction of the balloon. A cervical ripening balloon and or prostaglandins is/are inserted/administered, if the cervix is unripe (less than 2.5 cm dilated). Oxytocin can be started at any time for Induction or Augmentation during, before, or after use of cervical dilator balloon catheter of the present disclosure. A stylus is lubricated and is then inserted into the passageway of the shaft up to the end of the balloon to contact the silicone rubber padded tip of the balloon. The cervical dilator balloon catheter of the present disclosure is inserted, uninflated, through the cervix (that is over 1-2 cm dilated), guided by palpation or direct vision with a speculum. Ultrasound imaging is used, if needed, to guide or determine the position or path of the catheter tip. The stylus is removed and placed into the sterile tray. 30-40 cc saline is instilled into the balloon. The balloon is then retracted gently to confirm that the balloon's position is seated just inside the internal os of the cervix, in the lower uterine segment. If the position of the balloon is not certain, abdominal ultrasound scanning is used to confirm the position of the balloon. Inflation is increased to 150 cc saline. The balloon is then retracted through the cervical canal with strong gentle traction removing the inflated balloon and dilating the cervix to nearly 4 cm. The balloon and stylus are placed in the sterile tray with the balloon deflated. The cervix is checked with digital palpation to confirm the dilation. The uninflated balloon is reinserted, and the stylus is then carefully removed, and the balloon inflated with 30 cc saline. The balloon's position is reverified with retraction to see that the balloon is seated at the internal os, or, if available, an ultrasound is used to confirm. The stylus is removed and then, with the position of the balloon confirmed, the balloon is inflated to 300 cc. The Balloon again removed slowly, with gentle traction, and is placed on the sterile tray again. The cervix is checked and should be around 6 cm. The balloon is deflated, and the stylus replaced. The cervical dilator balloon catheter of the present disclosure is reinserted and inflated with 600 cc saline and may be checked again with ultrasound. The stylus is removed, and the balloon retracted with gentle traction outward and side to side and then anterior to posterior to gently remove the catheter while dilating the cervix, vagina and introitus. The outer sheath that forms a pocket for the balloon should make the removal easy by decreasing friction. Vaginal examination may now show the cervix to be completely dilated. If so, it's second stage labor. Now it's time to push. If the cervix is not completely dilated, the same sequential process of removing, reinserting, reinflating (increasing total injected by 150 cc more or less each time up to maximin total of 1000 cc) and checking the cervix after each inflation until the cervix is completely dilated.

Secondary use of the cervical dilator balloon catheter of the present disclosure includes situations, such as, for example, when a patient has stalled labor progress during a spontaneous labor or a stalled labor induction. In these cases, it's possible to use the cervical dilator balloon catheter of the present disclosure to augment the labor without increasing stress and fatigue. The balloon inflation volumes should be adjusted to match the diameters of cervical dilation, and a one-hour rest can be considered, if needed, after the first balloon is inserted. The sequential volumes of saline should correlate to the starting dilation. The balloon can have the shape of a sphere on top of a cone. Fetal heart rate monitoring should be used continuously throughout labor. The cervical dilation process should be paused, and the balloon deflated and removed, until any fetal distress can be diagnosed or resolved.

Goals/advantages of the system and method of the present disclosure can include: lower C-Section (CS) rate by as much as 30-50% (to <10-20%) 300,000 less CS in the US each year (can decrease 1000-2000/hospital/year); less CS for failure to progress; less CS for fetal distress sections; less fetal brain damage from asphyxia; less fetal brain damage from trauma Decreased amnionitis; less CS for failure to progress; less breech CS (second twin effect) if Obstetrician is skilled in breech extractions of a second twin or single breech and if 10-12 cm balloon is easily extracted; shorten length of labor; decrease vaginal and perineal trauma to mother; decreased maternal sepsis; decreased fetal sepsis; decreased maternal hemorrhage; decreased maternal deaths; decreased maternal postpartum depression; decreased pregnancy related hypertension; decreased preeclampsia; decreased eclampsia; decreased maternal cerebral hemorrhage; decrease fetal trauma to scalp, head and face; decreased fetal cerebral hemorrhage; decrease fetal distress by shortening labor, reducing the time length of opportunity for distress; reduce maternal blood loss by decreasing lacerations; decreased need for vacuum or forceps; decreased fetal cephalohematoma. Other goals/advantages of the system and method of the present disclosure are inherent from the structural features of the cervical dilation system, as well as the technical aspects of the method, as would be appreciated by one of ordinary skill in the art.

As discussed above, the system and method of the present disclosure can simulate a "Second Twin Effect". Indeed, since the first twin dilates the vagina and cervix there is no resistance for the birth of the second twin. So, the second twin slides easily through the dilated birth canal. This concept is simulated using the system and method of the present disclosure. However, instead of a first twin simulating the second twin effect, the cervical dilation system of the present disclosure is used to simulate the second twin effect using the method of the present disclosure. Indeed, the cervical dilation system of the present disclosure functions like the first twin. The cervical dilation system may include a balloon catheter having a conical shaped balloon dilator attached to a larger external thin and strong polyethylene sheath. Before or early in the labor, it is the Conical Balloon that dilates the vagina as it passes through the attached outer sheath with a very low friction coefficient reducing the amount of force needed to push the dilating balloon through. A closed sleeve is used that contains friction reducing silicone or other lubricant to almost 0 coefficient of friction. The balloon is pulled with an ergonomic yoke handle through that near 0 friction coefficient intussuscepting roller sleeve using minimal force. After gently pulling the balloon and sheath, there should be complete dilation of the cervix and vagina. Maternal pushing can begin with minimal resistance after opening the cervix and vagina. The mother can push the baby out with relative ease to deliver. Other alternative aids for delivery involve pulling and or attaching or grasping the baby's head and pulling with greater force which can result in trauma. These methods are known to cause severe injury to the baby's head, face and neck and are rarely used due to fear of lawsuits or injury. This is why the rate of C-Sections is growing rapidly and causing the complications of C-Sections to be exponentially rising. The most common reason for a C-Section is a previous C-Section. Because the uterus is weakened where a previous C-Section cut was made, it has a higher probability of rupture which can result in the fetal and/or maternal death.

In a first implementation of the invention, a cervical dilator comprises a shaft extending along a longitudinal axis between opposite proximal and distal ends. The shaft comprises opposite inner and outer surfaces. The inner surface defines a passageway. A balloon comprises a proximal end coupled to the proximal end of the shaft and an opposite distal end that is coaxial with the longitudinal axis. The balloon comprises an inner surface that defines a chamber. The chamber is in communication with the passageway. The shaft is configured to be coupled to an inflation source to move an inflation material through the passageway and into the chamber to move the balloon between an uninflated/unexpanded configuration in which the proximal head end of the balloon has a convex orientation an inflated/expanded configuration in which the proximal head end of the balloon has a concave orientation.

In a second aspect, the balloon is a reinforced silicone balloon.

In another aspect, the balloon is expandable to 12 cm in the inflated/expanded configuration.

In another aspect, the balloon is 1-2 cm in the uninflated/unexpanded configuration.

In another aspect, the balloon is narrow at the bottom and wide and spherical at the top.

In another aspect, the narrow bottom of the balloon is continuous with the spherical top of the balloon.

In another aspect, the narrow bottom of the balloon is tapered.

In another aspect, the narrow bottom of the balloon is sealed or plugged at the bottom.

In another aspect, the narrow bottom of the balloon is coupled to the shaft in an airtight and/or water-tight manner that prevents leakage of gas and/or liquid between the balloon and the shaft.

In another aspect, the inflation material is saline.

In another aspect, the distal end of the balloon is a disc.

In another aspect, the distal end of the balloon is disc-shaped.

In another aspect, the proximal end of the balloon is made from a first material and the distal end of the balloon is made from a second material that is different than the first material.

In another aspect, the proximal end of the balloon has a first thickness and the distal end of the balloon has a second thickness that is greater than the first thickness.

In another aspect, the shaft includes an optional handle for manipulating the shaft and/or the balloon relative to a patient.

In a second implementation of the invention, a cervical dilation system comprises a sleeve having an inner surface defining a cavity and opposite proximal and distal openings that are in communication with the cavity. A shaft extends along a longitudinal axis between opposite proximal and distal ends. The proximal end is positioned in the cavity adjacent to the distal opening. The shaft comprises opposite inner and outer surfaces. The inner surface of the shaft defines a passageway. A balloon comprises a proximal end coupled to the proximal end of the shaft and an opposite distal end that is coaxial with the longitudinal axis. The balloon comprises an inner surface that defines a chamber. The chamber is in communication with the passageway. The shaft is configured to be coupled to an inflation source to move an inflation material through the passageway and into the chamber to move the balloon between an uninflated/unexpanded configuration in which the proximal end of the balloon has a convex orientation an inflated/expanded configuration in which the distal end of the balloon has a concave orientation.

In another aspect, the inner surface of the sleeve is a portion of a first layer of the sleeve and the outer surface of the sleeve is a portion of a second layer of the sleeve, the sleeve including a channel between the first layer and the second layer.

In another aspect, an inner surface of the first layer and an inner surface of the second layer define the channel.

In another aspect, the sleeve includes a lubricant disposed the channel.

In another aspect, the lubricant has an extremely low coefficient of friction.

In another aspect, the lubricant is silicone.

In another aspect, the first layer and the second layer are constructed of low friction materials, such as, for example, polyethylene.

In another aspect, the sleeve is 11 cm in diameter.

In another aspect, the sleeve is a closed sleeve.

In another aspect, the sleeve is a Bursa sleeve.

In another aspect, the sleeve is slippery.

In another aspect, a top edge of the sleeve is slippery.

In another aspect, the sleeve is unattached at the bottom of the sleeve.

In another aspect, the sleeve includes tacking points that engage the balloon when the ballon is in the inflated/expanded configuration.

In another aspect, the tacking points couple the balloon to the sleeve and/or couple the sleeve to the balloon.

In another aspect, the cervical dilation system further includes a stylet configured to be movably positioned in the passageway such that the stylet engages the distal end of the balloon.

In another aspect, the stylus is configured for insertion of the balloon into a patient's cervix.

In another aspect, the stylus is semi-rigid.

In a third implementation of the invention, a method of cervical dilation comprises: providing a cervical dilator comprising: a sleeve comprising an inner surface defining a cavity and opposite proximal and distal openings that are in communication with the cavity, a shaft extending along a longitudinal axis between opposite proximal and distal ends, the proximal end being positioned in the cavity adjacent to the distal opening, the shaft comprising opposite inner and outer surfaces, the inner surface of the shaft defining a passageway, and a balloon comprising a proximal end coupled to the proximal end of the shaft and an opposite distal end that is coaxial with the longitudinal axis, the balloon comprising an inner surface that defines a chamber, the chamber being in communication with the passageway; inserting the cervical dilator into a patient such that the balloon is positioned in a cervix of the patient; coupling to an inflation source to the shaft and introducing inflation material from the inflation source into the passageway of the shaft to move the inflation material through the passageway and into the chamber and move the balloon from an uninflated/unexpanded configuration in which the distal end of the balloon has a convex orientation to an inflated/expanded configuration in which the distal end of the balloon has a concave orientation; and moving the balloon from the inflated/expanded configuration to the uninflated/unexpanded configuration.

In another aspect, the inflated/expanded configuration is a first inflated/expanded configuration and the method further comprises moving the balloon from the first inflated/expanded configuration to a second inflated/expanded configuration.

In another aspect, the balloon has a first diameter when the balloon is in the first inflated/expanded configuration and the balloon has a second diameter when the balloon is in the second inflated/expanded configuration.

In another aspect, the second diameter is greater than the first diameter.

In another aspect, the first diameter is about 3 cm and the second diameter is about 7 cm.

In another aspect, the first diameter is about 7 cm and the second diameter is about 10 cm.

In another aspect, the balloon is deflated before inflating the balloon to the second inflated/expanded configuration.

In another aspect, the balloon pressure and/or volume are monitored using a pressure gauge and/or volume meter.

In another aspect, the inflation material is introduced into the passageway via an electric or manual inflation pump.

In another aspect, the inflation material is introduced into the passageway via a syringe.

In a fourth implementation of the invention, a two-layered sleeve is constructed of low friction coefficient material and can contain a small amount of lubricant between the closed two layers. The containment of the lubricant by design is to prevent contact of lubricant to a patient or other person or thing while preserving the lubricant which is also enhanced by the low friction materials of the sleeve.

In a fifth implementation of the invention, a balloon of a conical shape of the bottom and a spherical shape of the top portion is provided in which the bottom portion is to increase the dilation of the vagina as it passes through, and the top spherical portion is to maintain and expand the dilation as it passes through exits.

In yet another example implementation, disclosed is a cervical dilation system comprising:

- a sleeve having an inner surface defining a cavity and opposite proximal and distal openings in communication with the cavity, the sleeve being constructed of a low friction material and configured to contain a lubricant between two layers of the sleeve to reduce friction during use;
- a shaft extending along a longitudinal axis between opposite proximal and distal ends, the shaft having an inner surface defining a passageway; and
- a balloon having a proximal end coupled to the proximal end of the shaft and a distal end spaced apart from the shaft, the balloon including an inner surface defining a chamber that is in fluid communication with the passageway,
- wherein the shaft is configured to be coupled to an inflation source to introduce an inflation material into the passageway and into the chamber to move the balloon between an uninflated configuration, in which the distal end has a convex orientation, and an inflated configuration, in which the distal end has a concave orientation,
- wherein inflation and movement of the balloon are configured to dilate a cervix, a vagina, and/or a vaginal introitus of a patient to simulate a first twin dilation effect.

In another aspect, the sleeve comprises an inner layer and an outer layer, the lubricant being disposed in a channel defined between the inner layer and the outer layer.

In another aspect, the lubricant comprises silicone and/or a water-soluble lubricant having an extremely low coefficient of friction.

In another aspect, the sleeve is constructed of polyethylene and/or another low-friction polymeric material.

In another aspect, the sleeve is a closed sleeve configured to contain the lubricant such that the lubricant does not contact a patient.

In another aspect, the balloon comprises a conical bottom portion and a spherical top portion, the conical bottom portion being configured to increase dilation as it passes through the cervix and the spherical top portion being configured to maintain and/or expand the dilation.

In another aspect, the spherical top portion of the balloon is configured to expand to a diameter of approximately 10 cm to 12 cm when fully inflated.

In another aspect, the balloon is expandable from approximately 1 cm to approximately 12 cm between the uninflated configuration and the inflated configuration.

In another aspect, the distal end of the balloon comprises a disc-shaped tip having a thickness greater than a thickness of a body portion of the balloon.

In another aspect, the disc-shaped tip is configured to cradle a fetal head during dilation.

In another aspect, the balloon comprises a reinforced silicone material that is compliant and/or semi-compliant.

In another aspect, the shaft includes one or more inflation ports in communication with the chamber to deliver the inflation material.

In another aspect, further comprising a stylet configured to be removably positioned in the passageway of the shaft to guide the balloon during insertion into the cervix.

In another aspect, the stylet is semi-rigid and includes a tip configured to engage an inner surface of the distal end of the balloon without piercing the balloon.

In another aspect, the sleeve and the balloon are configured to reduce friction to simulate a second twin effect by allowing a baby to pass through a fully dilated birth canal with minimal resistance.

In another aspect, the inflation source comprises a manual pump, an electric pump, and/or a syringe.

In another aspect, further comprising a pressure gauge and/or a volume meter configured to monitor a pressure and/or a volume of the inflation material within the balloon.

In another aspect, the system is configured to reduce labor time and decrease a need for a cesarean section by achieving full dilation of the cervix, the vagina, and the vaginal introitus.

In another implementation, disclosed is a method of dilating a cervix of a patient, the method comprising:

providing a cervical dilation system, the system comprising: a sleeve having an inner surface defining a cavity and opposite proximal and distal openings in communication with the cavity, the sleeve being constructed of a low friction material and configured to contain a lubricant between two layers of the sleeve to reduce friction during use;

a shaft extending along a longitudinal axis between opposite proximal and distal ends, the shaft having an inner surface defining a passageway; and a balloon having a proximal end coupled to the proximal end of the shaft and a distal end spaced apart from the shaft, the balloon including an inner surface defining a chamber that is in fluid communication with the passageway, wherein the shaft is configured to be coupled to an inflation source to introduce an inflation material into the passageway and into the chamber to move the balloon between an uninflated configuration, in which the distal end has a convex orientation, and an inflated configuration, in which the distal end has a concave orientation, wherein inflation and movement of the balloon are configured to dilate a cervix, a vagina, and/or a vaginal introitus of a patient to simulate a first twin dilation effect;

inserting the sleeve and the balloon into a birth canal of the patient with the balloon in the uninflated configuration;

coupling an inflation source to the shaft and introducing an inflation material comprising saline through the passageway into the chamber to inflate the balloon to a first diameter of about 3 cm to about 7 cm;

retracting the balloon to confirm seating of the balloon within the cervix;

further inflating the balloon to a second diameter of about 10 cm to about 12 cm;

sequentially reinserting, inflating, and removing the balloon to progressively dilate the cervix, the vagina, and the vaginal introitus; and removing the balloon to permit delivery of a baby through the fully dilated birth canal.

In another example implementation, disclosed is a cervical dilation device, comprising:

a two-layered sleeve formed of polyethylene, the sleeve having an inner layer and an outer layer defining a channel therebetween, the channel containing a silicone lubricant enclosed within the sleeve;

a shaft extending along a longitudinal axis between opposite proximal and distal ends, the shaft having a cylindrical passageway and one or more inflation ports; and a balloon coupled to the distal end of the shaft, the balloon comprising:

a narrow conical bottom portion configured for initial dilation, a wide spherical top portion configured for maintaining and expanding dilation, and a disc-shaped distal tip having a thickness greater than a thickness of a body portion of the balloon, wherein the balloon is inflatable from approximately 1 cm to approximately 12 cm using the inflation material delivered through the shaft, wherein the disc-shaped distal tip is configured to transition from a convex orientation when the balloon is uninflated to a concave orientation when the balloon is inflated, and wherein the sleeve and the silicone lubricant are configured to reduce friction during insertion, inflation, and removal of the balloon to simulate a second twin effect during labor.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

Figure 1:
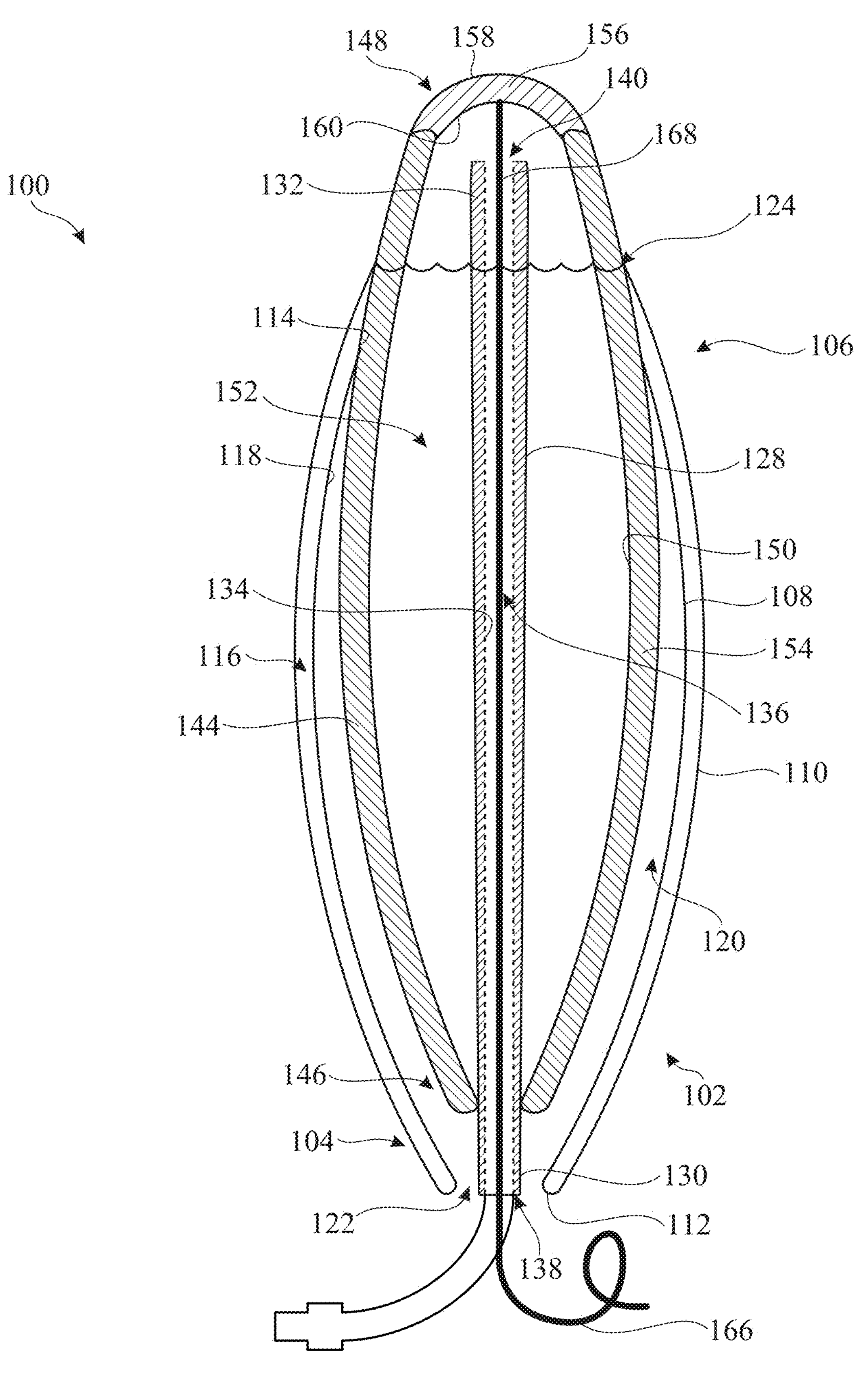
FIG. 1 presents a side, cross-sectional view of a cervical dilator of a cervical dilation system, in accordance with a first illustrative embodiment of the present invention, with a balloon of the cervical dilator in an uninflated configuration.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward cervical dilation systems and methods that simulate the dilation caused by a first twin to allow a baby to slide easily through the dilated birth canal.

Referring to FIGS. 1-7, a cervical dilation system 100, is illustrated in accordance with a first exemplary embodiment of the present invention. The cervical dilation system 100 includes a sheath, such as, for example, a sleeve 102. The sleeve 102 extends from a proximal end 104 to an opposite distal end 106. The sleeve 102 includes an inner wall, such as, for example, an inner layer 108 and an outer wall, such as, for example, an outer layer 110. The inner layer 108 and the outer layer 110 each extend continuously from the proximal end 104 to the distal end 106. The inner layer 108 is joined with the outer layer 110 at a junction 112 adjacent to the proximal end 104 and is joined with the outer layer at a junction 114 adjacent to the distal end 106 to define a cavity 116 between the inner layer 108 and the outer layer 110. In some embodiments, the cavity 116 is at least partially filled with a material, such as, for example, a lubricant. In some embodiments, the lubricant can include silicone. In some embodiments, the cavity 116 is closed so as to enclose the lubricant within the cavity 116 and prevent the lubricant from exiting the cavity 116. An inner surface 118 of the inner layer 108 defines a pocket 120 that is configured for disposal of a component of the cervical dilation system 100, such as, for example, a cervical dilation balloon catheter 126 of the cervical dilation system 100, as discussed hereinbelow. The sleeve 102 defines a proximal opening 122 adjacent the proximal end 104 and a distal opening 124 adjacent the proximal end 106. The proximal opening 122 and the distal opening 124 are configured for insertion and/or removal of the cervical dilation balloon catheter 126 into/from the sleeve 102, as also discussed hereinbelow.

In some embodiments, the sleeve 102 may be constructed of one or more low friction materials, such as, for example, polyethylene. It is contemplated that the low friction material that the sleeve 102 is made from, in combination with the lubricant contained within the cavity 116, will allows the cervical dilation balloon catheter 126 to propel through a birth canal smoothly with the least amount of friction or pressure. In some embodiments, the inner layer 108 may be loosely layered with the outer layer 110 to allow for relative movement between the inner layer 108 and the outer layer 110 during insertion, inflation, deflation and removal of the cervical dilation balloon catheter 126. In some embodiments, in order to perform the function(s) discussed herein, it is envisioned that all or part of the sleeve 102 may be fabricated from and/or coated with a pliable, low-friction material, such as, for example, silicone, polyurethane, silicone-polyurethane copolymers, polymeric rubbers, polyolefin rubbers, elastomers, rubbers, thermoplastic elastomers, thermoset elastomers and elastomeric composites.

Figure 2:
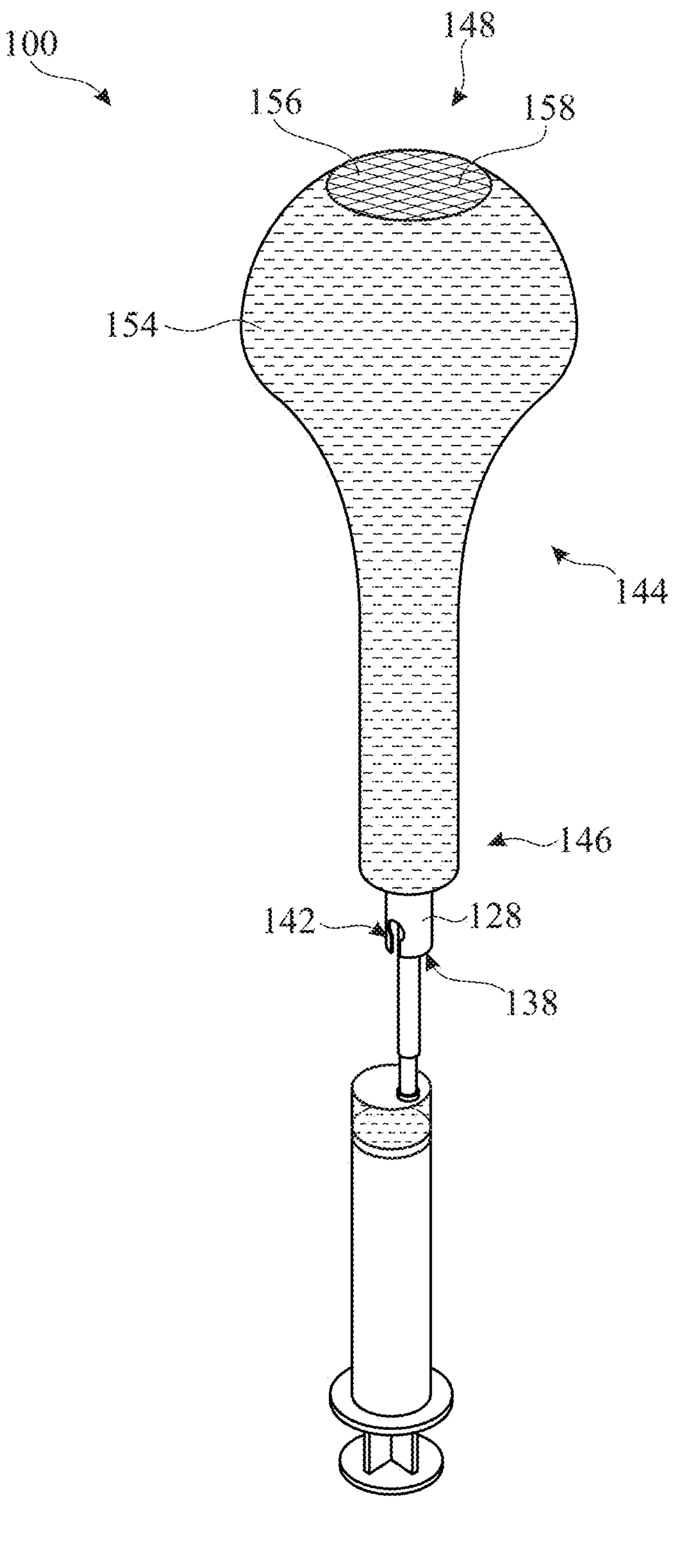
FIG. 2 presents a perspective view of components of the cervical dilation system illustrated in FIG. 1, with the balloon of the cervical dilator in a partially inflated/expanded configuration.

The cervical dilation balloon catheter 126 of the cervical dilation system 100 includes a hollow tube, such as, for example, a shaft 128. The shaft 128 extends between a proximal end 130 and an opposite distal end 132. An inner surface 134 of the shaft 128 defines a channel 136. The shaft 128 defines a proximal opening 138 adjacent to the proximal end 130 and a distal opening 140 adjacent the distal end 132. The channel 136 is configured for movable disposal of a stylet and/or filling tube of the cervical dilation system 100, as discussed herein. The proximal opening 138 and the distal opening 140 are each in communication with the channel 136. In some embodiments, the shaft 128 has a linear configuration such that the proximal opening 138 is coaxial with the distal opening 140. In some embodiments, the shaft 128 may include a mating feature 142 configured to couple the shaft 128 to another component, such as, for example, a pump or syringe, as discussed herein below. In one particular embodiment, the mating feature 142 is a notch or cutout having an arcuate portion and a linear portion, as shown in FIG. 2. In some embodiments, all or part of the shaft 128 is made from a rigid material or a semi-rigid material, such as, for example, polyethylene. In some embodiments, the channel 136 has a uniform diameter along the entire length of the shaft 128. In some embodiments, the channel 136 has a circular and/or cylindrical cross-sectional configuration. In some embodiments, the channel 136 may have various cross-sectional configurations, such as, for example, oval, oblong, triangular, rectangular, square, polygonal, irregular, uniform, nonuniform, variable, tubular and/or tapered.

In one embodiment, shown in FIGS. 1-5, the cervical dilation balloon catheter 126 of the cervical dilation system 100 includes a balloon 144 that is coupled to shaft 128 and configured to move between inflated and uninflated configurations in use of the cervical dilation system 100 to simulate the dilation caused by a first twin and allow a baby to slide easily through the dilated birth canal, as discussed herein. The balloon 144 includes a proximal end 146 that is coupled to the proximal end 130 of the shaft 128 and an opposite distal end 148. The proximal end 146 may be coupled to the shaft 128 in any manner known in the art, such as, for example, sonic welding, adhesive, etc. The distal end 148 of the balloon 144 is spaced apart from the shaft 128 and is positioned such that at least a portion of the distal end 148 is coaxial with the shaft 128 and/or the channel 136 when the balloon 144 is in the inflated configuration. The balloon 144 includes an inner surface 150 that defines a chamber 152. The chamber 152 is in communication with channel 136 of the shaft 128 via the distal opening 140 of the shaft 128 such that an inflation source, such as, for example, a pump, syringe, etc. can be coupled to the proximal end 130 of the shaft 128 to move an inflation material, such as, for example, saline through the proximal opening 138 and the channel 136 such that the inflation material exits the channel 136 through the distal opening 140 of the shaft and fills the chamber 152 to move the balloon 144 from an uninflated/unexpanded configuration to an inflated/expanded configuration or from a partially inflated/expanded configuration to a more fully inflated/expanded configuration.

It is envisioned that the balloon 144 can be variously sized and shaped. For example, in some embodiments, the balloon 144 may be adapted to have a size and shape that conforms to that of a female birth canal such that the balloon 144 can be introduced into the birth canal to dilate the birth canal upon inflation/expanded of the balloon 144, or sequential inflation/expansion of the balloon 144, as discussed herein. In some embodiments, the balloon 144 has a conical or substantially conical shape at the distal end 148 of the balloon 144 and the balloon 144 can have a tubular shape at the proximal end 146 of the balloon 144. In some embodiments, the balloon 144 can be narrow at the proximal end 146 of the balloon 144 and can be wide and spherical at the distal end 148 of the balloon 144. Other shapes are contemplated. For example, all or a portion of the balloon 144 can be variously shaped, such as, for example, oval, oblong, triangular, square, polygonal, irregular, uniform, non-uniform, offset, staggered, undulating, arcuate, variable and/or tapered.

In some embodiments, the balloon 144 is made from a resilient biocompatible material. In some embodiments, the balloon 144 is a thick reinforced silicone balloon. In one embodiment, the balloon 144 is a compliant balloon that resists stretching. In one embodiment, the balloon 144 is a non-compliant or semi-compliant balloon that stretches, at least to some degree. Whether the balloon 144 is a compliant balloon or a non-compliant balloon, it is envisioned that the balloon 144 is capable of expanding to large diameters upon inflation of the balloon 144. In some embodiments, at least a portion of the proximal end 146 of the balloon 144 is made from a first material and at least a portion of the distal end 148 of the balloon 144 is made from a second material that is different from the first material that at least a portion of the proximal end 146 of the balloon 144 is made from. For example, a body 154 of the balloon 144 may be made from the first material and a distal tip 156 of the balloon 144 may be made from the second material. In some embodiments, the distal tip 156 may be in the form of a disc or substantially in the form of a disc. In some embodiments, the first and second materials each include silicone. In some embodiments, the first and second materials each consist of silicone. However, it is envisioned that the thickness of the second material is greater than the thickness of the first material, thus making the second material different than the first material. For example, the first material that forms the body 154 of the balloon 144 can have a first thickness and the second material that forms the tip 156 of the balloon 144 can have a second thickness that is greater than the first thickness. In some embodiments, the second thickness is 25% to 1000% greater than the first thickness. In one embodiment, the second thickness is 50% to 500% greater than the first thickness. In one embodiment, the second thickness is 100% to 250% greater than the first thickness. In one embodiment, the second thickness is 200% greater than the first thickness. In one embodiment, the second thickness is 150% greater than the first thickness. It is noted that for methods that require the tip 156 to be engaged with a stylus to manipulate the cervical dilation balloon catheter 126 relative to a patient, that the second thickness must be thick enough to prevent being pierced or punctured by the stylus, as discussed herein.

Figure 3:
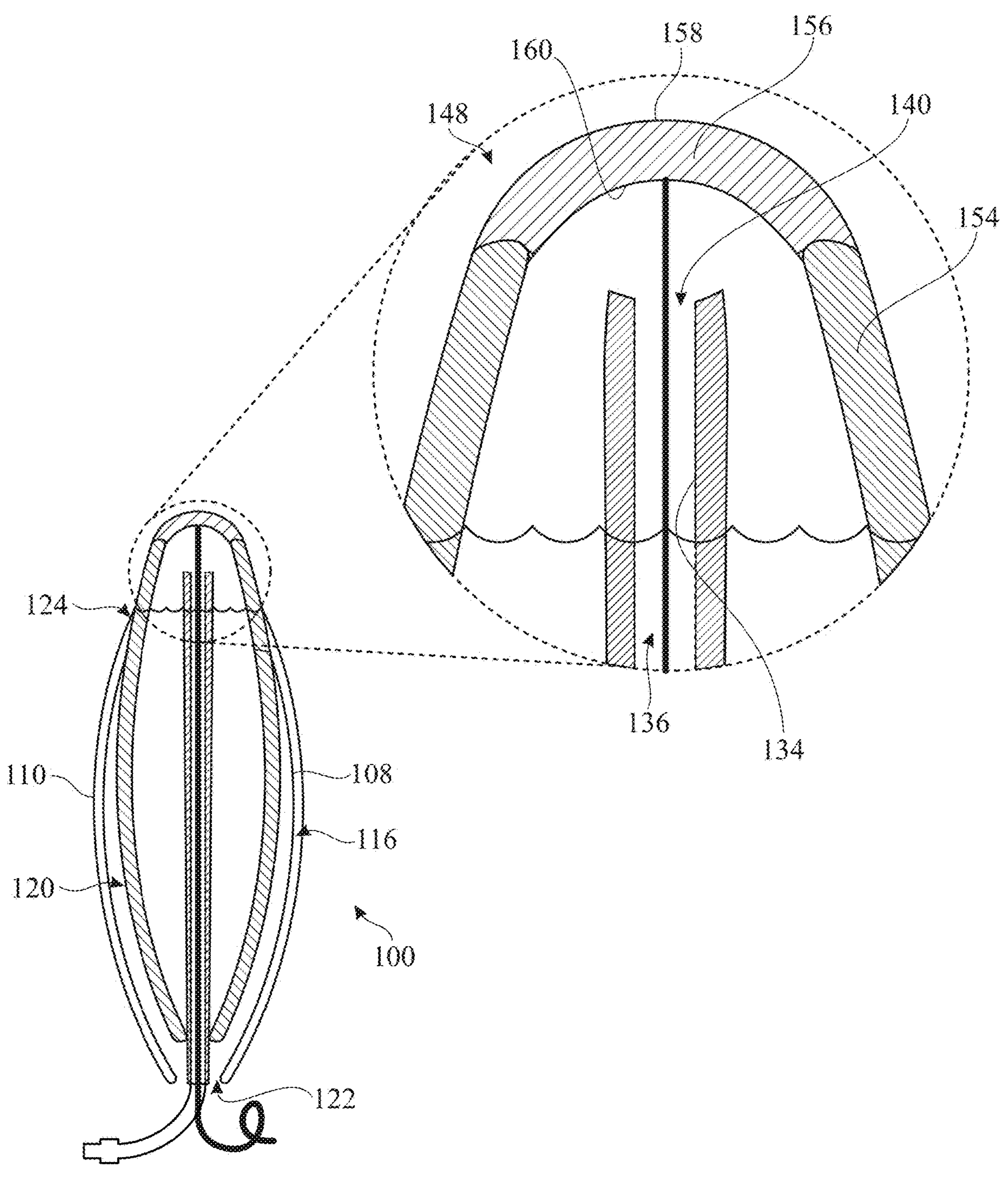
FIG. 3 presents an enlarged detailed view of a portion of the cervical dilator illustrated in FIG. 1.
Figure 4:
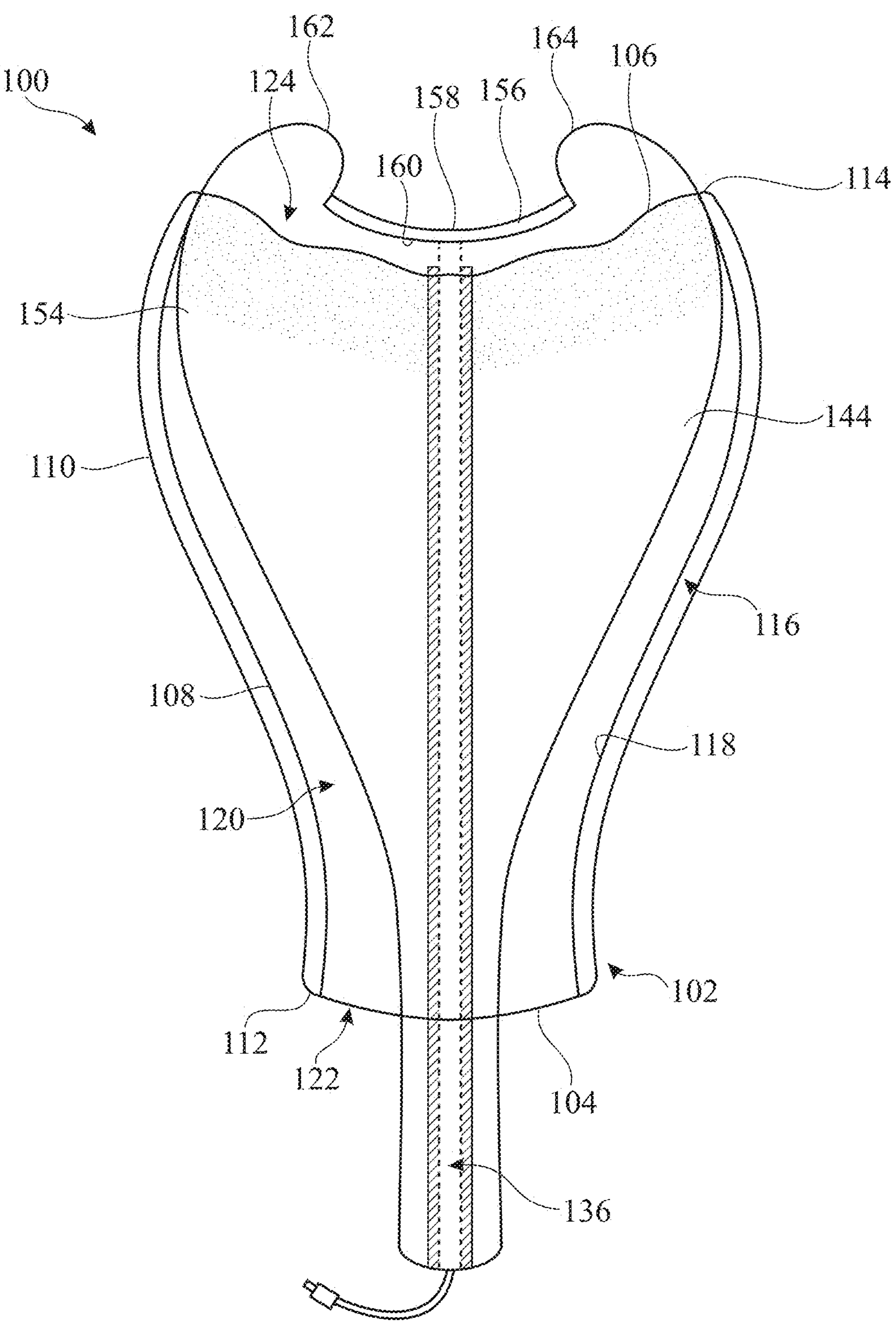
FIG. 4 presents a side, cross-sectional view, of the cervical dilation system illustrated in FIG. 1, with the balloon of the cervical dilator in a fully inflated/expanded configuration.
Figure 5:
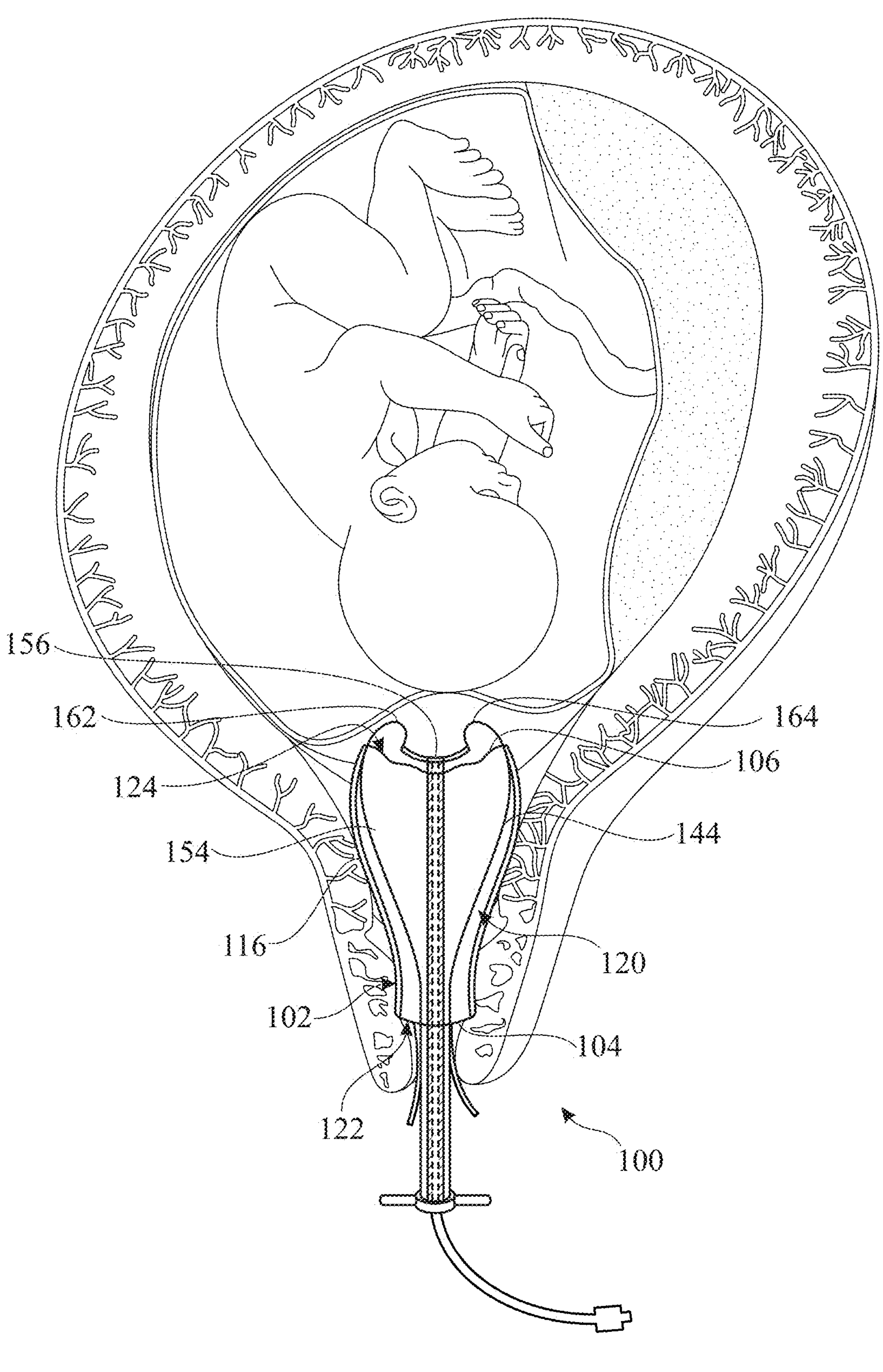
FIG. 5 presents a plan view of the cervical dilation system illustrated in FIG. 1 in use, with the balloon of the cervical dilator in a first inflated/expanded configuration.

As would be appreciated by one of ordinary skill in the art, by having the tip 156 of the balloon 144 made from the second material such that the tip 156 has second thickness and having the body 154 of the balloon 144 made from the first material such that the body 154 has the reduced first thickness effects the performance of the balloon 144. For example, the varying thicknesses of the balloon 144 will affect the shape of the balloon 144 when the balloon 144 expands upon inflation of the balloon 144. In this case, when the balloon 144 is in an uninflated or unexpanded configuration, or when the balloon 144 is in a partially inflated or expanded configuration, the distal end 148 of the balloon 144 (the tip 156) will have a convex configuration, as shown in FIGS. 1-3. That is, an outer surface 158 of the tip 156 is convex and an opposite inner surface 160 of the tip 156 is concave to define the convex configuration of the distal end 148/tip 156. However, as the balloon 144 is inflated, the balloon 144 will move from the uninflated or expanded configuration to an inflated or expanded configuration, or from the partially inflated or expanded configuration to the inflated or expanded configuration. As the balloon 144 moves from the uninflated or expanded configuration to an inflated or expanded configuration, or from the partially inflated or expanded configuration to the inflated or expanded configuration, the distal end 148/tip 156 moves from the convex configuration to a concave configuration, as shown in FIGS. 4 and 5. In particular, the outer surface 158 of the tip 156 is concave and the inner surface 160 of the tip 156 is convex to define the concave configuration of the distal end 148/tip 156. As discussed herein, inflating/expanding the balloon 144 such that the distal end 148/tip 156 has the concave configuration is functional to cradle a baby's head. That is, the concave configuration of the distal end 148/tip 156 provides a cavity in which the baby's head can be positioned as the mother's cervix is dilated.

In some embodiments, inflating/expanding the balloon 144 such that the distal end 148/tip 156 has the concave configuration results in the body 154 forming a lobe 162, as shown in FIGS. 4 and 5, wherein the distal end 148/tip 156 is recessed inwardly from a distal end 164 of the lobe 162. In some embodiments, the lobe 162 extends circumferentially about the distal end 148/tip 156 such that the distal end 148/tip 156 is positioned between the distal end 164 of the lobe 162 and the proximal end 146 of the balloon 144. In some embodiments, the lobe 162 is arcuate. However, other shapes are contemplated. It is envisioned that lobe 162 can function to maintain the baby's head within the cavity defined by the concave configuration of the distal end 148/tip 156. That is, when the balloon 144 is inflated/expanded such that the distal end 148/tip 156 has the concave configuration, the lobe 162 will form around the baby's head, to maintain the baby's head within the cavity defined by the concave configuration of the distal end 148/tip 156. In some embodiments, the lobe 162 together with the tip 156 combine to define the concave configuration of the distal end 148/tip 156.

Figure 6:
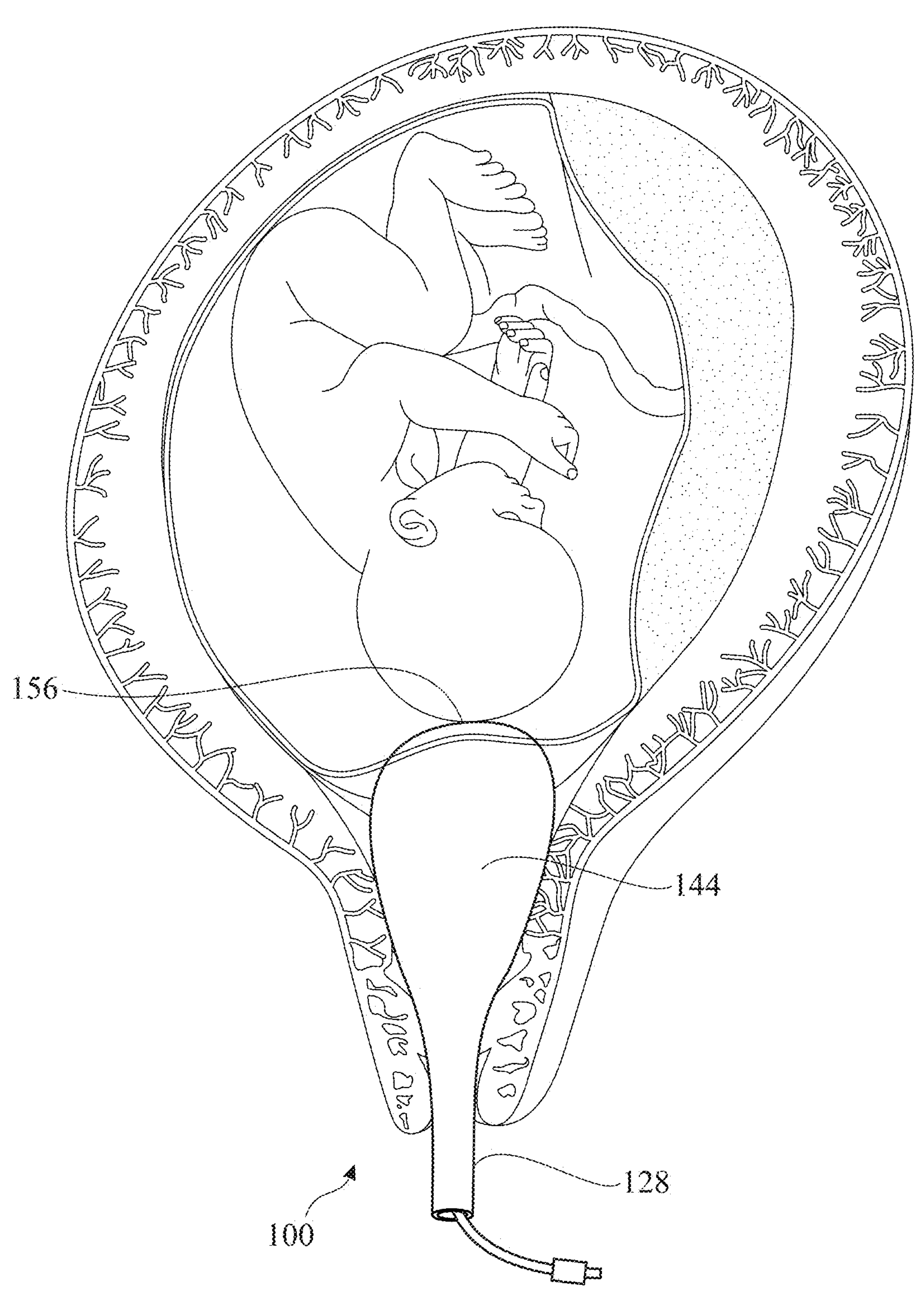
FIG. 6 presents a plan view of the cervical dilation system illustrated in FIG. 1 in use, with the balloon of the cervical dilator in a second inflated/expanded configuration.
Figure 7:
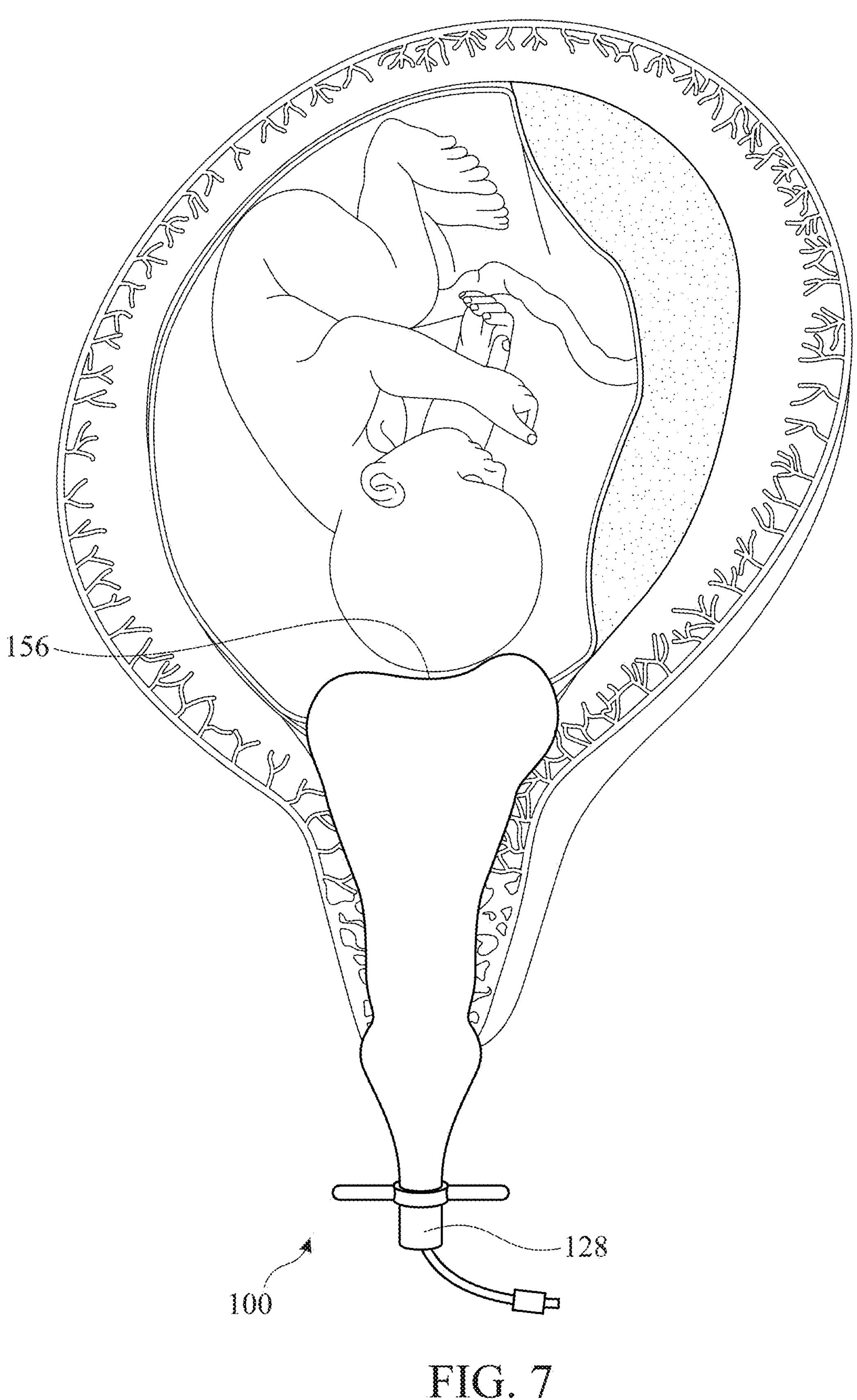
FIG. 7 presents a plan view of the cervical dilation system illustrated in FIG. 1 in use, with the balloon of the cervical dilator in a third inflated/expanded configuration.

In operation and use, referring now to FIGS. 5-7, the cervical dilation system 100 may be used to simulate the dilation caused by a first twin to allow a baby to slide easily through the dilated birth canal. In particular, to dilate the cervix of a patient, such as, for example, a mother who is about to give birth to a baby using the cervical dilation system 100, a needle or tube is inserted into the patient and the patient is administered an antibiotic for prophylaxis intravenously through the needle or tube to prevent infection. Intravenous administration of the antibiotic is maintained for hydration during labor and delivery. The patient can be attached to a continuous fetal monitor. A physical exam may be performed on the mother, in which fetal weight and position may be estimated, for example. The patient may obtain epidural anesthesia for comfort during labor and insertion/retraction of the sleeve 102 and/or the cervical dilation balloon catheter 126.

Figure 10:
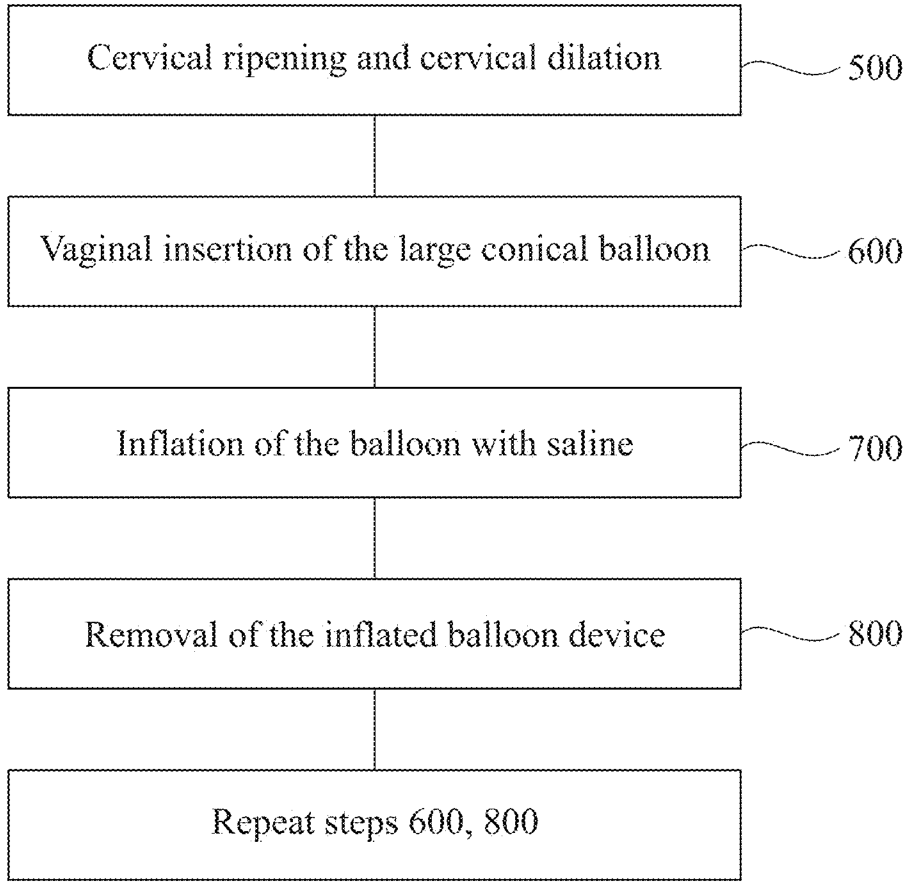
FIG. 10 presents a flow chart illustrating steps used in conducting one embodiment of a method for cervical dilation.

After the patient obtains anesthesia, the balloon 144 may be inserted into the patient's cervix without pain, with the balloon 144 in the uninflated or unexpanded configuration, or the balloon 144 in the partially inflated or partially inflated configuration, as shown in FIGS. 1-3. The insertion of the balloon 144 can be represented as a step 500, as shown in FIG. 10. In some cases, the patient may be administered prostaglandins, if needed. Oxytocin can be started at any time for induction or augmentation during, before, or after use of the balloon 144. However, prior to the insertion of the cervical dilation balloon catheter 126 into the patient's cervix, the sleeve 102 may be positioned within the patient's cervix to assist with insertion and removal of the cervical dilator balloon catheter 126 into and from the patient's cervix as well as to assist during inflation and deflation of the balloon 144. Indeed, due to the lubricant disposed in the cavity 116 of the sleeve 102 as well as the low friction material of the inner layer 108 and the outer layer 110 of the sleeve 102, the sleeve 102 will allow the balloon 144 to move easily within the patient's cervix, reducing potential bodily damage and trauma.

To insert the balloon 144 into the patient's cervix, a stylus 166 can be lubricated and inserted through the proximal opening 138, the channel 136 and the distal opening 140 of the shaft 128 such that a tip 168 of the stylus 166 engages the distal tip 156 of the balloon 144, prior to inserting the balloon 144 into the patient. In some embodiments, the tip 168 of the stylus 166 contacts the inner surface 160 of the tip 156 of the balloon 144 without piercing or puncturing the inner surface 160. Once the tip 168 of the stylus 166 contacts the tip 156 of the balloon 144, the balloon 144 (in the uninflated or unexpanded configuration, or in the partially inflated or partially inflated configuration) is guided through the cervix, which is over 2 cm dilated, by palpation or direct vision with a speculum. Ultrasound imaging may be used, if needed, to guide or determine the position or path of the catheter tip 156.

The stylus 166 is removed and placed into the sterile tray. 30-40 cc of saline is instilled into the balloon 144 by coupling a pump or syringe, for example to the proximal end 130 of the shaft 128 such that the pump or syringe directs an inflation material, such as, for example, saline through the channel 136 and the distal opening 140 of the shaft 128 and the saline fills the chamber 152 of the balloon 144 to expand the balloon 144. The expansion/inflation of the balloon 144 can be represented as a step 600, as shown in FIG. 10. Following expansion of the balloon 144, the balloon 144 may be retracted gently to confirm that the balloon 144 is seated just inside the internal os of the cervix in the lower uterine segment. If the position of the balloon 144 is not certain, ultrasound scanning may be used to confirm the position of the balloon 144.

Once the proper positioning of the balloon 144 is confirmed, by retraction and/or ultrasound, inflation with saline is increased to 150 cc to expand the balloon 144 a second time. Following the second expansion of the balloon 144, the balloon 144 may be deflated by moving at least some of the saline within the chamber 152 of the balloon out of the chamber 152 and through the shaft 128 such that the saline exits the shaft 128 through the proximal opening 138 of the shaft 128. In some embodiments, all of the saline in the chamber 152 is removed to minimize the size of the balloon 144 during removal of the cervical dilator balloon catheter 126 from the cervix. Following inflation of the balloon 144, the balloon 144 is retracted through the cervical canal with strong gentle traction, thus removing the balloon 144 and dilating the cervix to nearly 4 cm. The cervical dilator balloon catheter 126 is placed in the sterile tray with the stylus 166. The patient's cervix may be checked with digital palpation to confirm the dilation.

The balloon 144, while still deflated, is reinserted into the patient's cervix with the tip 168 of the stylus 166 engaging the tip 156 of the balloon 144, as discussed above. The stylus 166 is disengaged from the balloon 144 and is removed from the cervical dilator balloon catheter 126. The balloon 144 is then inflated with 30 cc of saline to expand the balloon 144 a fourth time. The position of the balloon 144 following inflation with 30 cc of saline can be verified with retraction to ensure that the balloon 144 is seated at the internal os. Ultrasound scanning may be used to confirm the position of the balloon 144, in place of, or in addition to, retraction of the balloon 144. With position confirmed, the balloon is inflated to 300 cc with saline to further expand the balloon 144 and cause further dilation of the cervix. Following inflating/expanding the balloon 144 with 300 cc of saline, the balloon 144 is removed again slowly, with gentle traction. The cervical dilator balloon catheter 126 is deflated and placed on the sterile tray again. The cervix can be checked and should be around 6 cm.

Next, the balloon 144 is gently reinserted into the patient's cervix and inflated with 600 cc saline. That is, inflating the balloon 144 with the 600 cc of saline further inflates/expands the balloon 144. The positioning of the balloon 144 may be checked with retraction of the balloon 144 and/or ultrasound. Following inflating/expanding the balloon 144 with the 600 cc of saline, the balloon 144 is removed with gentle traction outward and side to side and then anterior to posterior to gently remove the cervical dilation balloon catheter 126 while dilating the cervix, vagina and introitus. The removal of the cervical dilator balloon catheter 126 can be represented as a step 800, as shown in FIG. 10. The sleeve 102 makes the removal of the cervical dilation balloon catheter 126 easy by decreasing friction. Vaginal exams may now show cervix to be completely dilated. If so, it's second stage labor which means that the mother can complete labor by pushing the baby out easily through the opened birth canal. The cervical ripening and dilation can be represented as a step 700, as shown in FIG. 10.

If the patient's cervix is not completely dilated however, the same sequential process of removing and reinserting the balloon 144 and reinflating the balloon 144 can be repeated. However, the total injections of saline can be increased by 150 cc each time up, to maximin total of 1000 cc. As before, the position of the balloon 144 in the cervix is checked after each inflation, until the cervix is completely dilated.

Referring to FIGS. 8A-9B, a cervical dilation system 200, is illustrated in accordance with a second exemplary embodiment of the present invention. The cervical dilation system 200 includes a sheath, such as, for example, the sleeve 102. When used with cervical dilation system 200, pocket 120 that is configured for disposal of a component of the cervical dilation system 200, such as, for example, a cervical dilation balloon catheter 226 of the cervical dilation system 200. The cervical dilation balloon catheter 226 of the cervical dilation system 200 includes a shaft 228. The shaft 228 extends between a proximal end 230 and an opposite distal end 232. An inner surface 234 of the shaft 228 defines a channel 236. The shaft 228 defines a proximal opening 238 adjacent to the proximal end 130. The distal end 232, however, is closed and does not include any openings. The channel 236 is configured for movable disposal of a stylet and/or filling tube of the cervical dilation system 200, as discussed herein. The proximal opening 238 is in communication with the channel 236.

The cervical dilation balloon catheter 226 of the cervical dilation system 200 includes a balloon 244 that is coupled to shaft 228 and configured to move between inflated/expanded and uninflated/unexpanded configurations in use of the cervical dilation system 200 to simulate the dilation caused by a first twin and allow a baby to slide easily through the dilated birth canal, as discussed herein. The balloon 244 includes a proximal end 246 that is coupled to the proximal end 230 of the shaft 228 and an opposite distal end 248. The proximal end 246 may be coupled to the shaft 228 in any manner known in the art, such as, for example, sonic welding, adhesive, etc. The distal end 248 of the balloon 244 is spaced apart from the shaft 228 and is positioned such that at least a portion of the distal end 248 is coaxial with the shaft 228 and/or the channel 236 when the balloon 244 is in the inflated/expanded configuration. The balloon 244 includes an inner surface 250 that defines a chamber 252. The shaft 228 can include one or a plurality of inflation ports 240 that extend through shaft 128 and are in communication with the channel 236 and the chamber 252 such that an inflation source, such as, for example, a pump, syringe, etc. can be coupled to the proximal end 230 of the shaft 228 to move an inflation material, such as, for example, saline through the proximal opening 238 and the channel 236 such that the inflation material exits the channel 236 through the inflation ports 140 of the shaft 228 and fills the chamber 252 to move the balloon 244 from the uninflated or unexpanded configuration to the inflated or expanded configuration or from a partially inflated or expanded configuration to a more fully inflated or expanded configuration.

It is envisioned that the balloon 244 can be variously sized and shaped. For example, in some embodiments, the balloon 244 may be adapted to have a size and shape that conforms to that of a female birth canal such that the balloon 244 can be introduced into the birth canal to dilate the birth canal upon inflation of the balloon 244, as discussed herein. In some embodiments, the balloon 244 has a conical or substantially conical shape at the distal end 248 of the balloon 244 and the balloon 244 can have a tubular shape at the proximal end 246 of the balloon 244. In some embodiments, the balloon 244 can be narrow at the proximal end 246 of the balloon 244 and can be wide and spherical at the distal end 248 of the balloon 244. Other shapes are contemplated. For example, all or a portion of the balloon 244 can be variously shaped, such as, for example, oval, oblong, triangular, square, polygonal, irregular, uniform, nonuniform, offset, staggered, undulating, arcuate, variable and/or tapered.

Figure 8A:
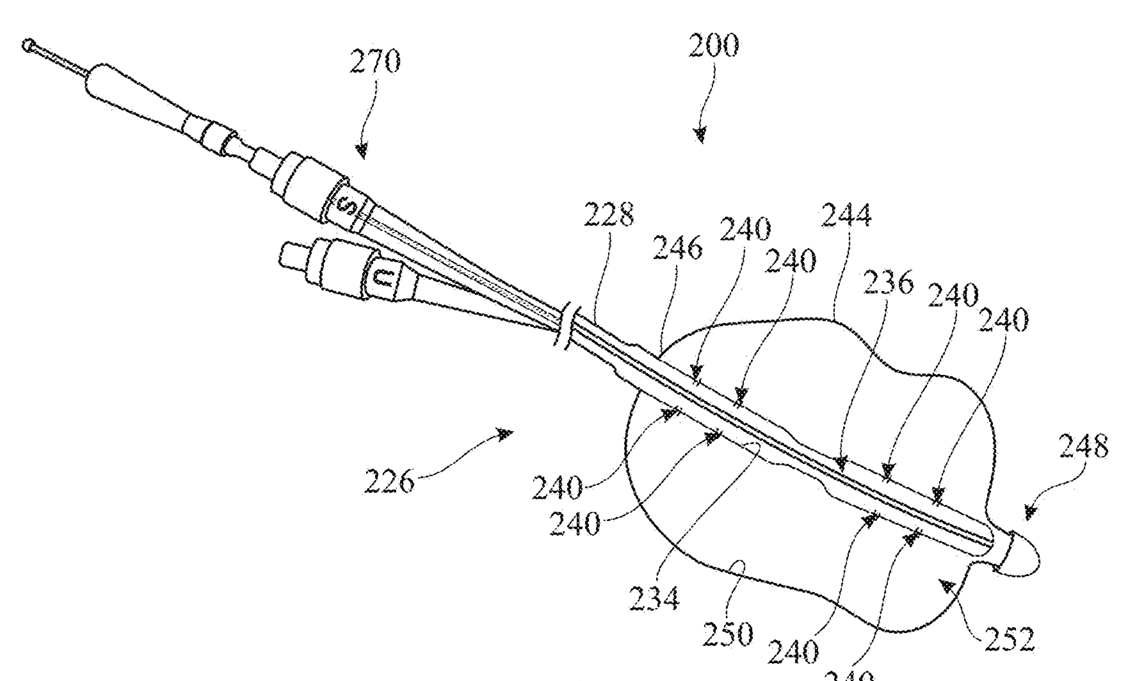
FIG. 8A presents a perspective, cross-sectional view of a cervical dilation system having a cervical dilator, with a balloon of the cervical dilator in a first inflated/expanded configuration.
Figure 8B:
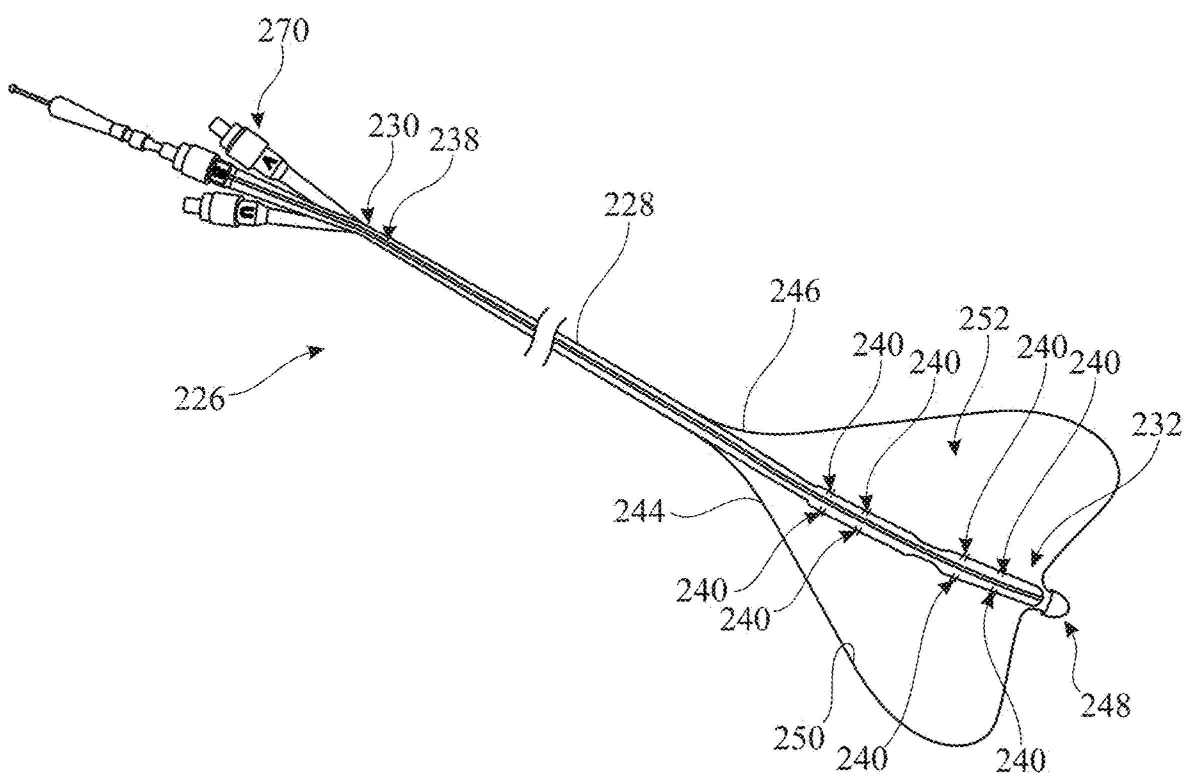
FIG. 8B presents a perspective, cross-sectional view of the cervical dilation system illustrated in FIG. 8A, with the balloon of the cervical dilator in a second inflated/expanded configuration.

In some embodiments, the balloon 244 is made from a resilient biocompatible material. In some embodiments, the balloon 244 is a thick reinforced silicone balloon. In one embodiment, the balloon 244 is a compliant balloon that resists stretching. In one embodiment, the balloon 244 is a non-compliant or semi-compliant balloon that stretches, at least to some degree. Whether the balloon 244 is a compliant balloon or a non-compliant balloon, it is envisioned that the balloon 244 is capable of expanding to large diameters upon inflation of the balloon 244. As would be appreciated by one of ordinary skill in the art, the balloon 244 can be manufactured to have a specific shape when the balloon 244 expands upon inflation of the balloon 244. In some embodiments, the balloon 244 has a thickened conical tip 256 that remains conical prior to inflation/expansion of the balloon 244 (FIG. 8A) and following inflation/expansion of the balloon 244 (FIG. 8B). A body 254 of the balloon 244 thus expands as the balloon 244 is inflated to change the size and shape of the body 254 of the balloon 244, while the tip 256 remains conical.

In operation and use, the cervical dilation system 200 may be used to simulate the dilation caused by a first twin to allow a baby to slide easily through the dilated birth canal. In particular, to dilate the cervix of a patient, such as, for example, a mother who is about to give birth to a baby using the cervical dilation system 200, a needle or tube is inserted into the patient and the patient is administered an antibiotic for prophylaxis intravenously through the needle or tube to prevent infection. Intravenous administration of the antibiotic is maintained for hydration during labor and delivery. The patient can be attached to a continuous fetal monitor. A physical exam may be performed on the mother, in which fetal weight and position may be estimated, for example. The patient may obtain epidural anesthesia for comfort during labor and insertion/retraction of the sleeve 102 and/or the cervical dilation balloon catheter 226.

Figure 9A:
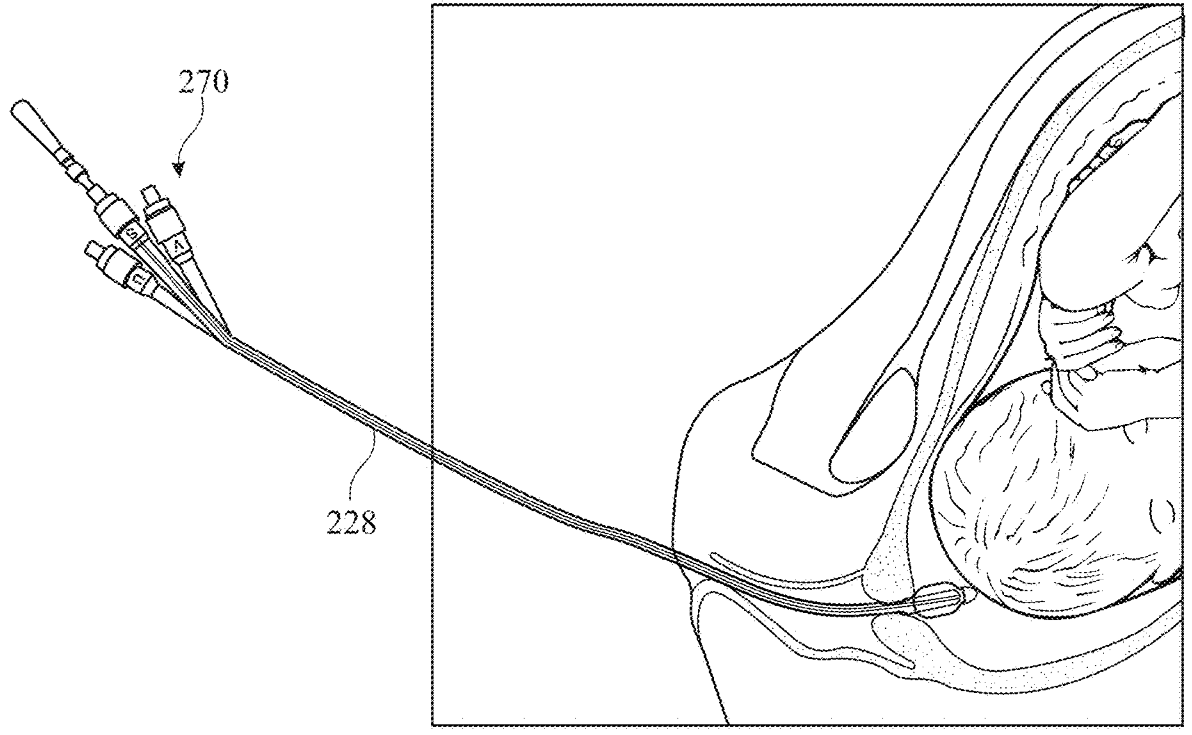
FIG. 9A presents a plan view of the cervical dilation system illustrated in FIG. 8A in use, with the balloon of the cervical dilator in the first inflated/expanded configuration.
Figure 9B:
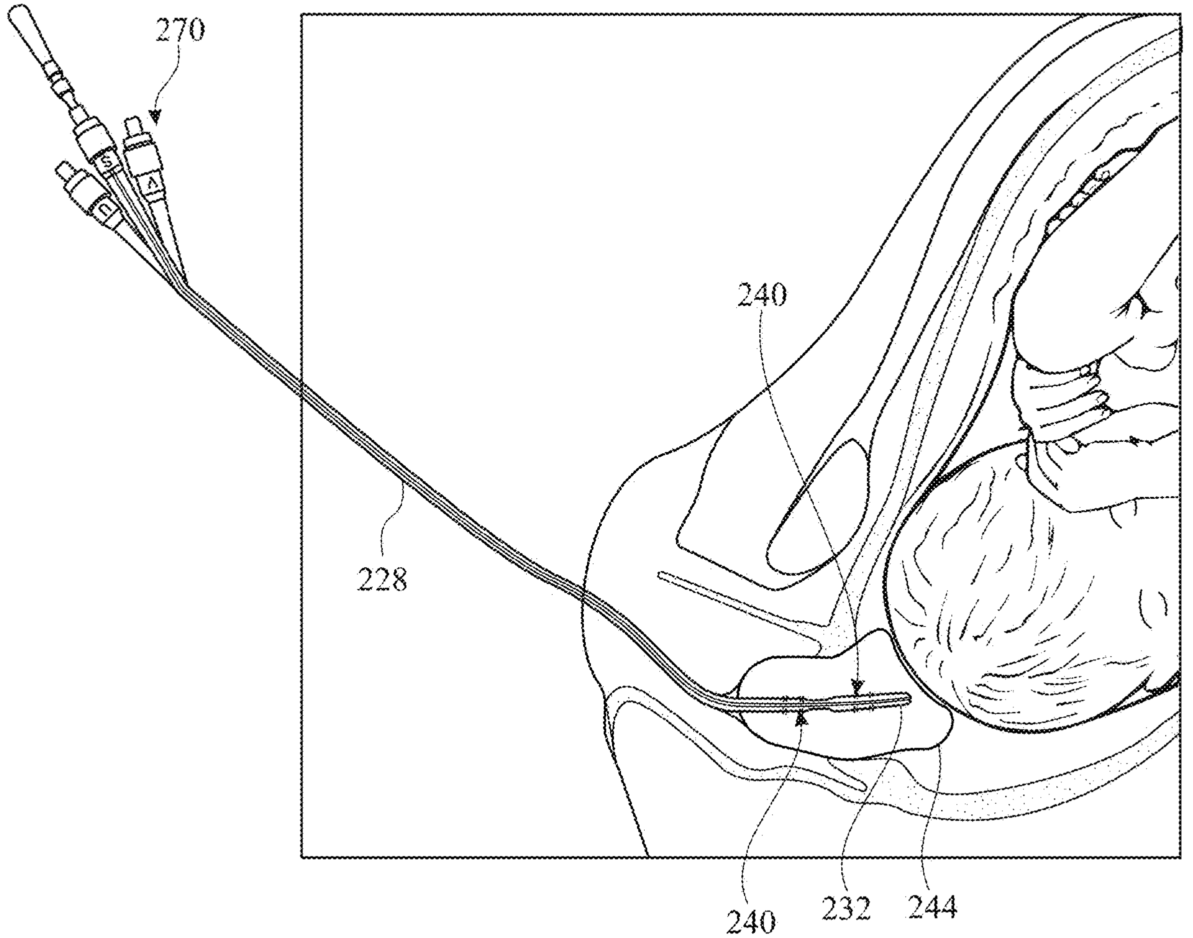
FIG. 9B presents a plan view of the cervical dilation system illustrated in FIG. 8A in use, with the balloon of the cervical dilator in the second inflated/expanded configuration.

After the patient obtains anesthesia, cervical ripening and cervical dilation is performed, as discussed hereinabove. Cervical ripening and cervical dilation can be represented as a step 500, as shown in FIG. 10. Following cervical ripening and cervical dilation, the balloon 244 may be inserted into the patient's cervix, with the balloon 244 in the uninflated or unexpanded configuration, or the balloon 244 in the partially inflated or partially inflated configuration, as shown in FIG. 9A. The insertion of the balloon 244 can be represented as a step 600, as shown in FIG. 10. In some cases, the patient may be administered prostaglandins, if needed. Oxytocin can be started at any time for induction or augmentation during, before, or after use of the balloon 244. However, prior to the insertion of the cervical dilation balloon catheter 226 into the patient's cervix, the sleeve 102 may be positioned within the patient's cervix to assist with insertion and removal of the cervical dilator balloon catheter 226 into and from the patient's cervix as well as to assist during inflation and deflation of the balloon 244. Indeed, due to the lubricant disposed in the cavity 116 of the sleeve 102 as well as the low friction material of the inner layer 108 and the outer layer 110 of the sleeve 102, the sleeve 102 will allow the balloon 244 to move easily within the patient's birth canal, reducing potential bodily damage and trauma.

To insert the balloon 244 into the patient's cervix, a stylus 266 can be lubricated and inserted through the proximal opening 238 and into the channel 236 of the shaft 228 such that a tip 268 of the stylus 266 engages the distal end of the shaft 228, prior to inserting the balloon 244 into the patient. Once the tip 268 of the stylus 266 contacts the distal end of the shaft 228, the balloon 244 (in the uninflated or unexpanded configuration, or in the partially inflated or partially inflated configuration) is guided through the cervix, which is over 2 cm dilated, by palpation or direct vision with a speculum. Ultrasound imaging may be used if needed to guide or determine the position or path of the balloon 244.

The stylus 266 is removed and placed into the sterile tray. 30-40 cc of saline is instilled into the balloon 244 by coupling a pump or syringe, for example to the proximal end 230 of the shaft 228 and/or a connector 270 that is coupled to the proximal end 230 of the shaft 228 such that the pump or syringe directs an inflation material, such as, for example, saline through the channel 236 and the inflation ports 240 of the shaft 128 and the saline fills the chamber 252 of the balloon 244 to expand the balloon 244. The expansion/inflation of the balloon 244 can be represented as the step 700, as shown in FIG. 10. Following expansion of the balloon 244, the balloon 244 may be retracted gently to confirm that the balloon 244 is seated just inside the internal os of the cervix in the lower uterine segment. If the position of the balloon 244 is not certain, ultrasound scanning may be used to confirm the position of the balloon 244.

Once the proper positioning of the balloon 244 is confirmed, by retraction and/or ultrasound, inflation with saline is increased to 150 cc to expand the balloon 244 a second time. Following the second expansion of the balloon 244, the balloon 244 may be deflated by moving at least some of the saline within the chamber 252 of the balloon out of the chamber 252 and through the shaft 228 such that the saline exits the shaft 228 through the proximal opening 238 of the shaft 228. In some embodiments, all of the saline in the chamber 252 is removed. Following inflation of the balloon 244, the balloon 244 is retracted through the cervical canal with strong, yet gentle traction, removing the balloon 244 and dilating the cervix to nearly 4 cm. The cervical dilator balloon catheter 226 is placed in the sterile tray with the stylus 266. The patient's cervix may be checked with digital palpation to confirm the dilation.

The balloon 244, while still deflated, is reinserted into the patient's cervix with the tip 268 of the stylus 266 engaging the distal end 232 of the shaft 228, as discussed above. The stylus 266 is disengaged from the shaft 228 and is removed from the cervical dilator balloon catheter 226. The balloon 244 is then inflated with 30 cc of saline to expand the ballon 244 a third time. The position of the balloon 244 following inflation with 30 cc of saline can be verified with retraction to ensure that the balloon 244 is seated at the internal os. Ultrasound scanning may be used to confirm the position of the balloon 244 in place of, or in addition to, retraction of the balloon 244. With the position of the balloon 244 confirmed, the balloon 244 is inflated to 300 cc with saline. The balloon 244 is removed again slowly, with gentle traction, and is placed on the sterile tray again. The cervix can be checked and should be around 6 cm. The balloon 244 is deflated and the stylus 266 is replaced.

Next, the balloon 214 is gently reinserted into the patient's cervix and inflated with 600 cc saline. That is, inflating the balloon 244 with the 600 cc of saline further inflates/expands the balloon 244. The positioning of the balloon 244 may be checked with retraction of the balloon 244 and/or ultrasound. Following inflating/expanding the balloon 244 with the 600 cc of saline, the balloon 244 is removed with gentle traction outward and side to side and then anterior to posterior to gently remove the cervical dilation balloon catheter 226 while dilating the cervix, vagina and introitus. The removal of the cervical dilator balloon catheter 226 can be represented as the step 800, as shown in FIG. 10. The sleeve 202 makes the removal of the cervical dilation balloon catheter 226 easy by decreasing friction. Vaginal exams may now show cervix to be completely dilated. If so, it's second stage labor, which means that the mother can complete labor by pushing. The cervical ripening and dilation can be represented as the step 500, as shown in FIG. 10. Followed by the step 6 insertion of the large conical balloon.

If the patient's cervix is not completely dilated however, the same sequential process of removing and reinserting the balloon 244 and reinflating the balloon 244, with increasing total injected by 150 cc each time up to maximin total of 1000 cc. That is, the cervical ripening and cervical dilation of step 500, the vaginal insertion of the large conical balloon of step 600, the inflation of the balloon with saline of step 700 and the removal of the inflated balloon of step 800 may be repeated in a step 900, until dilation is complete, as shown in FIG. 10. As before, the position of the balloon 244 in the cervix is checked after each inflation until the cervix is completely dilated.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A cervical dilation system comprising:

a sleeve having an inner surface defining a cavity and opposite proximal and distal openings in communication with the cavity, the sleeve being constructed of a low friction material and configured to contain a lubricant between two layers of the sleeve to reduce friction during use;

a shaft extending along a longitudinal axis between opposite proximal and distal ends, the shaft having an inner surface defining a passageway; and a balloon having a proximal end coupled to the proximal end of the shaft and a distal end spaced apart from the shaft, the balloon including an inner surface defining a chamber that is in fluid communication with the passageway, wherein the shaft is configured to be coupled to an inflation source to introduce an inflation material into the passageway and into the chamber to move the balloon between an uninflated configuration, in which the distal end has a convex orientation, and an inflated configuration, in which the distal end has a concave orientation, wherein inflation and movement of the balloon are configured to dilate a cervix, a vagina, and/or a vaginal introitus of a patient to simulate a first twin dilation effect.

2. The system of claim 1, wherein the two layers of the sleeve comprises an inner layer and an outer layer, the lubricant being disposed in a channel defined between the inner layer and the outer layer.

3. The system of claim 2, wherein the lubricant comprises silicone and/or a water-soluble lubricant having an extremely low coefficient of friction.

4. The system of claim 1, wherein the sleeve is constructed of polyethylene and/or another low-friction polymeric material.

5. The system of claim 1, wherein the sleeve is a closed sleeve configured to contain the lubricant such that the lubricant does not contact a patient.

6. The system of claim 1, wherein the balloon comprises a conical bottom portion and a spherical top portion, the conical bottom portion being configured to increase dilation as it passes through the cervix and the spherical top portion being configured to maintain and/or expand the dilation.

7. The system of claim 6, wherein the spherical top portion of the balloon is configured to expand to a diameter of approximately 10 cm to 12 cm when fully inflated.

8. The system of claim 1, wherein the balloon is expandable from approximately 1 cm to approximately 12 cm between the uninflated configuration and the inflated configuration.

9. The system of claim 1, wherein the distal end of the balloon comprises a disc-shaped tip having a thickness greater than a thickness of a body portion of the balloon.

10. The system of claim 9, wherein the disc-shaped tip is configured to cradle a fetal head during dilation.

11. The system of claim 1, wherein the balloon comprises a reinforced silicone material that is compliant and/or semi-compliant.

12. The system of claim 1, wherein the shaft includes one or more inflation ports in communication with the chamber to deliver the inflation material.

13. The system of claim 1, further comprising a stylet configured to be removably positioned in the passageway of the shaft to guide the balloon during insertion into the cervix.

14. The system of claim 13, wherein the stylet is semi-rigid and includes a tip configured to engage an inner surface of the distal end of the balloon without piercing the balloon.

15. The system of claim 1, wherein the sleeve and the balloon are configured to reduce friction to simulate a second twin effect by allowing a baby to pass through a fully dilated birth canal with minimal resistance.

16. The system of claim 1, wherein the inflation source comprises a manual pump, an electric pump, and/or a syringe.

17. The system of claim 1, further comprising a pressure gauge and/or a volume meter configured to monitor a pressure and/or a volume of the inflation material within the balloon.

18. The system of claim 1, wherein the system is configured to reduce labor time and decrease a need for a cesarean section by achieving full dilation of the cervix, the vagina, and the vaginal introitus.

19. A method of dilating a cervix of a patient, the method comprising:

providing a cervical dilation system, the system comprising: a sleeve having an inner surface defining a cavity and opposite proximal and distal openings in communication with the cavity, the sleeve being constructed of a low friction material and configured to contain a lubricant between two layers of the sleeve to reduce friction during use;

a shaft extending along a longitudinal axis between opposite proximal and distal ends, the shaft having an inner surface defining a passageway; and a balloon having a proximal end coupled to the proximal end of the shaft and a distal end spaced apart from the shaft, the balloon including an inner surface defining a chamber that is in fluid communication with the passageway, wherein the shaft is configured to be coupled to an inflation source to introduce an inflation material into the passageway and into the chamber to move the balloon between an uninflated configuration, in which the distal end has a convex orientation, and an inflated configuration, in which the distal end has a concave orientation, wherein inflation and movement of the balloon are configured to dilate a cervix, a vagina, and/or a vaginal introitus of a patient to simulate a first twin dilation effect;

inserting the sleeve and the balloon into a birth canal of the patient with the balloon in the uninflated configuration;

coupling an inflation source to the shaft and introducing an inflation material comprising saline through the passageway into the chamber to inflate the balloon to a first diameter of about 3 cm to about 7 cm;

retracting the balloon to confirm seating of the balloon within the cervix;

further inflating the balloon to a second diameter of about 10 cm to about 12 cm;

sequentially reinserting, inflating, and removing the balloon to progressively dilate the cervix, the vagina, and the vaginal introitus; and removing the balloon to permit delivery of a baby through the fully dilated birth canal.

20. A cervical dilation device, comprising:

a two-layered sleeve formed of polyethylene, the sleeve having an inner layer and an outer layer defining a channel therebetween, the channel containing a silicone lubricant enclosed within the sleeve;

a shaft extending along a longitudinal axis between opposite proximal and distal ends, the shaft having a cylindrical passageway and one or more inflation ports; and a balloon coupled to the distal end of the shaft, the balloon comprising:

a narrow conical bottom portion configured for initial dilation, a wide spherical top portion configured for maintaining and expanding dilation, and a disc-shaped distal tip having a thickness greater than a thickness of a body portion of the balloon, wherein the balloon is inflatable from approximately 1 cm to approximately 12 cm using the inflation material delivered through the shaft, wherein the disc-shaped distal tip is configured to transition from a convex orientation when the balloon is uninflated to a concave orientation when the balloon is inflated, and wherein the sleeve and the silicone lubricant are configured to reduce friction during insertion, inflation, and removal of the balloon to simulate a second twin effect during labor.

* * * * *